United States Patent [19]
Horvath

[11] Patent Number: 6,124,340
[45] Date of Patent: Sep. 26, 2000

[54] POLYMORPHIC COMPOUNDS

[75] Inventor: Karol Horvath, Södertälje, Sweden

[73] Assignee: Astra Aktiebolag, Sodertalje, Sweden

[21] Appl. No.: 08/875,203

[22] PCT Filed: Jun. 18, 1997

[86] PCT No.: PCT/SE97/01097

§ 371 Date: Jul. 31, 1997

§ 102(e) Date: Jul. 31, 1997

[87] PCT Pub. No.: WO97/49681

PCT Pub. Date: Dec. 31, 1997

[30] Foreign Application Priority Data

Jun. 24, 1996 [SE] Sweden ................................. 9602477
Mar. 3, 1997 [SE] Sweden ................................. 9700751

[51] Int. Cl.$^7$ ....................... A61K 31/405; C07D 209/12
[52] U.S. Cl. ............................................ 514/419; 548/491
[58] Field of Search ............................... 514/419; 548/491

[56] References Cited

U.S. PATENT DOCUMENTS 4,739,073   4/1988   Kathawala .............................. 548/406

FOREIGN PATENT DOCUMENTS 0114027   7/1984   European Pat. Off. .
0547000   6/1993   European Pat. Off. .

*Primary Examiner*—Joseph K. McKane
*Attorney, Agent, or Firm*—White & Case LLP

[57] ABSTRACT

This invention relates to a novel form of the HMG-CoA reductase inhibitor fluvastatin, more specifically to a highly crystalline form of fluvastatin sodium, referred to as fluvastatin sodium form B. The invention also relates to processes for production of fluvastatin sodium form B, to pharmaceutical compositions comprising fluvastatin sodium form B, and to the use of fluvastatin sodium form B in medical treatment.

23 Claims, 3 Drawing Sheets

Fig. 5
(a)
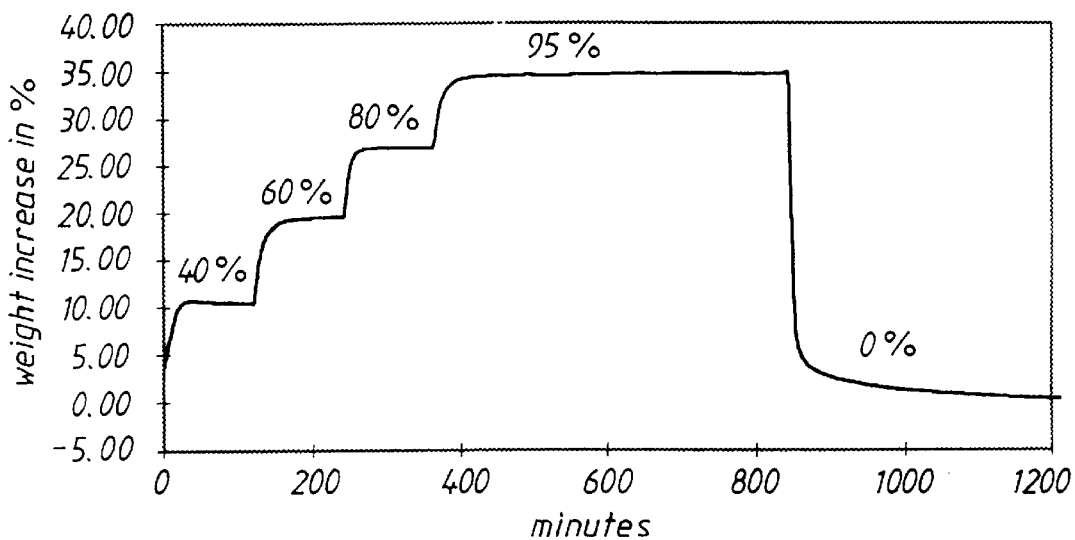
(b)
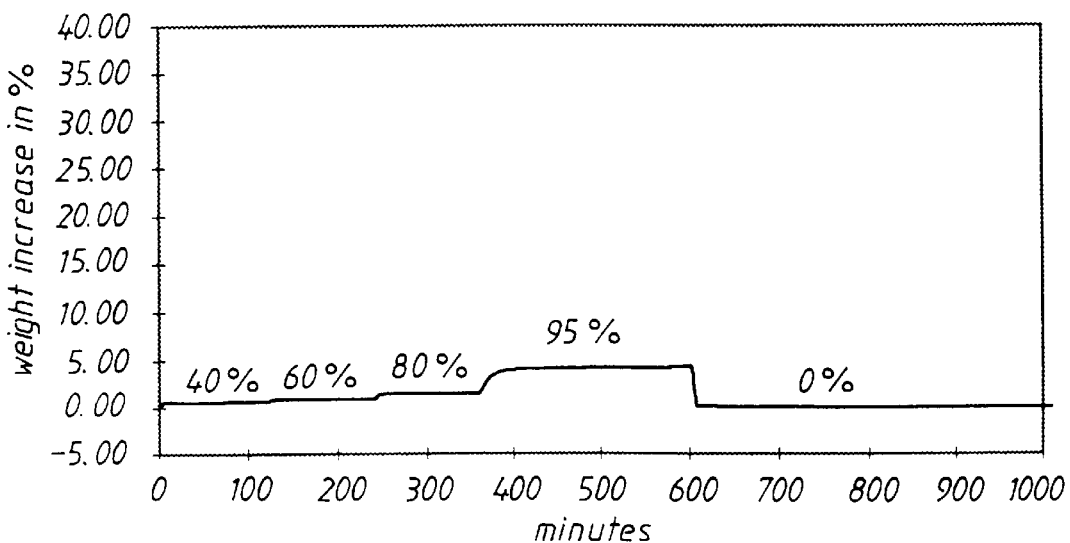

POLYMORPHIC COMPOUNDS

This application is a 371 of PCT/SE97/01097 filed Jun. 18, 1997.

TECHNICAL FIELD

This invention relates to a novel form of the HMG-CoA reductase inhibitor fluvastatin, more specifically to a highly crystalline form of fluvastatin sodium, referred to as fluvastatin sodium form B. The invention also relates to processes for production of fluvastatin sodium form B, to pharmaceutical compositions comprising fluvastatin sodium form B, and to the use of fluvastatin sodium form B in medical treatment

BACKGROUND ART

Fluvastatin, of which the full chemical name is R*, S*-(E)-(±)-7-[3-(4-fluorophenyl)-1-(1-methyl-ethyl)-1H-indol-2-yl]-3,5-dihydroxy-6-heptenoic acid, as well as its sodium salt, are disclosed in EP-A-0 114 027. Fluvastatin is an inhibitor of 3-hydroxy-3-methyl-glutaryl coenzyme A (HMG-CoA) reductase, which is a key enzyme in the regulation of cholesterol biosynthesis. Fluvastatin can be used pharmaceutically particularly as a hypercholesterolemic, hyperlipoproteinemic and antiatherosclerotic agent Fluvastatin sodium recovered by lyophilization is disclosed in U.S. Pat. No. 4,739,073.

In EP-A-0 547 000 it is disclosed that fluvastatin sodium is extremely susceptible to degradation at pH below about 8. The suggested solution is to provide compositions comprising the drug substance and an alkaline medium, which is capable of by imparting a pH of at least 8 to an aqueous solution or dispersion of the composition.

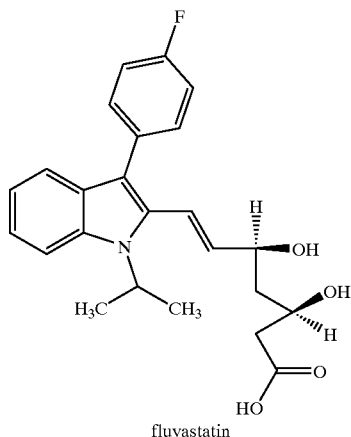

fluvastatin

It is pointed out in EP-A-547 000 that, in addition to the pH sensitivity, the heat and light sensitivity, as well as the hygroscopicity, of fluvastatin sodium impose particular requirements on the manufacture and storage of pharmaceutical dosage forms of fluvastatin sodium. It is known in the art that lower hygroscopicity will lead to improved chemical stability and longer shelf life of chemical compounds.

Consequently, there is a need for new forms of fluvastatin sodium having improved chemical stability, making possible the preparation of pharmaceutical formulations of fluvastatin sodium with less need for stabilizing agents and with prolonged shelf life, and with the possibility of being provided in less sophisticated packages.

BRIEF DESCRIPTION OF THE DRAWINGS

FIG. 5: Water sorption/desorption profiles: (a) fluvastatin sodium form A; (b) fluvastatin sodium form B.

DISCLOSURE OF THE INVENTION

Figure 1:
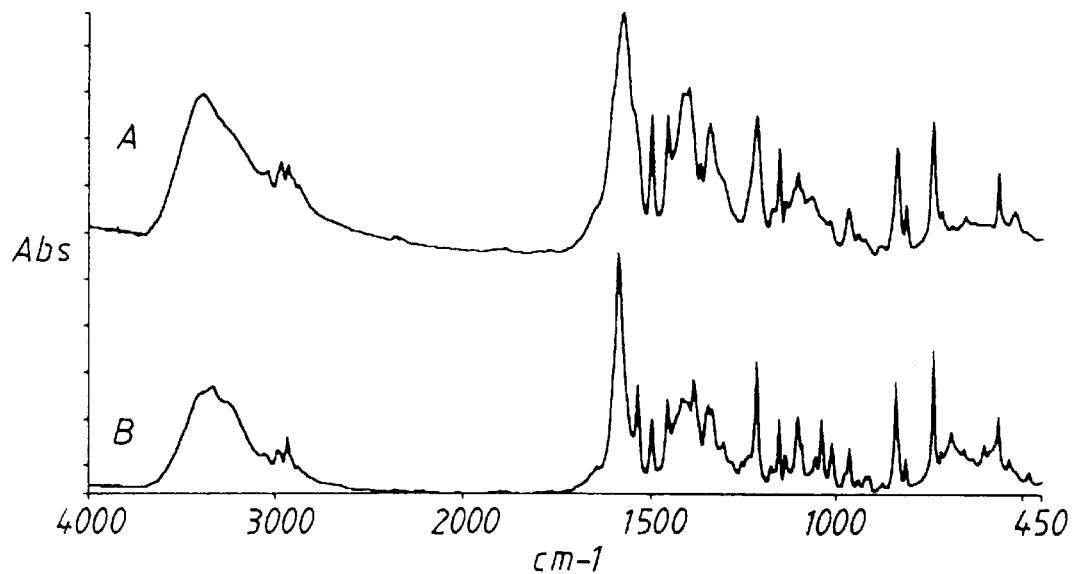
FIG. 1: FT-IR absorbance spectra of fluvastatin sodium (A) form A and (B) form B. Abscissa scale: 4000–450 cm$^{-1}$. Ordinate scale: Absorbance maximum 0.66 at 1577 cm$^{-1}$ for spectrum A, 1.11 at 1587 cm$^{-1}$ for spectrum B.

We have found that lyophilization of fluvastatin sodium yields a mixture of a crystalline form and amorphous material. The crystalline form comprised in this mixture is referred to as fluvastatin sodium form A. It has surprisingly been shown that fluvastatin sodium can crystallize in a new crystalline form, hereinafter referred to as fluvastatin sodium form B.

Fluvastatin sodium form B is a novel form of polymorphic fluvastatin sodium which has several advantageous properties compared with previously known forms of fluvastatin sodium:

it is less hygroscopic than fluvastatin sodium form A and amorphous fluvastatin sodium;

it has improved stability against light exposure.

It is predicted that these advantageous properties will lead to improved chemical stability and longer shelf life both for the pure substance and for pharmaceutical dosage forms containing fluvastatin sodium form B. Consequently, there will be less need for the addition of stabilizing agents in pharmaceutical dosage forms and fewer demands on packages, in particular on the water permeability and light transmission. Packages can thus be made of materials that are less complicated and more environmental friendly, for instance blister packs can be made of transparent material so that the tablets can be visible and the total package is smaller than in the case of aluminium blister packs.

Characteristics of Fluvastatin Sodium Form B

The novel form of fluvastatin sodium of the invention, i.e. form B, can be distinguished from form A by methods such as infra-red spectroscopy and powder X-ray diffractometry.

In a first aspect, the invention thus provides a novel form of fluvastatin sodium preferably substantially crystallographically pure fluvastatin sodium form B. A crystallographically pure form is a crystal modification that, as far as can be judged from PXRD measurements, contain no peaks from other crystal modifications. The term "substantially crystallographically pure fluvastatin sodium form B" should thus be understood as fluvastatin sodium form B containing only small amounts of any other crystalline form of fluvastatin sodium; preferably not more than 5% and most preferably not more than 3%, of any other crystalline form of fluvastatin sodium. The term "form" is in this context equivalent to the term "crystal modification".

Fluvastatin sodium form B can be characterized by an infra-red spectrum showing peaks at 3343, 2995, 1587, 1536, 1386, 1337, 1042, and 1013 cm$^{-1}$ which are characteristic for fluvastatin sodium form B and not found for form A.

Fluvastatin sodium form B can also be characterized by the X-ray powder diffraction pattern as described in the experimental Section 2.2 below.

Preparation of Fluvastatin Sodium Form B

In a further aspect, the invention relates to a process for the preparation of fluvastatin sodium form B. Fluvastatin sodium form B may be prepared under controlled conditions from a mixture of one or more organic solvents and water. It is preferred to use a mixture of organic solvents, which is miscible with water. The optimal ratio of organic solvents and water in the mixture to obtain form B is strongly dependent on the characteristics of the chosen organic solvents and the process conditions e.g. the temperature, the pressure and the solubility of fluvastatin sodium in each of the solvents, as well as in the mixture of the solvents.

In particular, fluvastatin sodium form B can be prepared by one of the following methods:

(i) Transformation of polymorphs in a slurry. Any non-B form of fluvastatin sodium, e.g. amorphous material or fluvastatin sodium form A, can initially be partly dissolved in the organic solvent and water mixture and stirred until the desired form B is formed. The process comprises a transformation in the slurry without a complete dissolution of the starting material. Such transformation may occur, as it is known in the art, when there exists a form with higher thermodynamic stability at the prevailing conditions. The driving force for the process is the normally lower solubility of the more stable form.

(ii) Reaction crystallization in an organic solvent system and water, with a suitable sodium compound, preferably an aqueous solution of sodium hydroxide or sodium carbonate. The starting material is e.g. the corresponding free acid, or the ester or a salt of fluvastatin. The composition of the resulting mixture after addition of the reactant should be such that it contains the ratio of organic solvents and water required for formation of fluvastatin sodium form B. The crystallization may start spontaneously, but it is preferable to add seeds of fluvastatin sodium form B.

(iii) Crystallization from a solution of fluvastatin sodium in a mixture of organic solvents and water. The starting solution of fluvastatin sodium can be formed either by dissolution of already isolated fluvastatin sodium, or it can be formed in a previous process step where fluvastatin sodium is formed by chemical reaction. The solution may become supersaturated with respect to form B due to the lower solubility of this form and crystallization of form B can therefore occur spontaneously. However, if the original solution is undersaturated with respect to form B, crystallization may be induced by decreasing the solubility of fluvastatin sodium in the system e.g. by cooling the mixture, by evaporating some of the solvents or by mixing with, e.g. by adding, some precipitating solvent Mixing with a precipitating solvent is particularly advantageous in that it offers a larger flexibility in the selection of solvents that can result in the required solvent mixture in which the desired form B of fluvastatin sodium may be formed. It also offers a faster process and a better control of the process such as yield and filterability. The water content in the final mixture is critical, but adjustment to the required solvent/water ratio can be done at any time in the process, e.g. during or after mixing with a precipitating solvent.

When the starting material for the crystallization of fluvastatin sodium is already isolated fluvastatin sodium form A or B, the process can be described as follows:

Fluvastatin sodium is dissolved in one or more organic solvents, preferably polar organic solvents, most preferably methanol or ethanol. In order to dissolve the starting material completely, it may be helpful to warm the solvents or to add a small amount of water to the solvent system. The amount of solvent mixture should be sufficiently high to dissolve all the fluvastatin sodium but should not be so large that the volumes involved become uneconomic. The preferred amount of solvent mixture is 2–20 ml/g fluvastatin sodium, most preferably 3–10 ml/g. It is preferable that the total mixture is agitated, e.g. stirred, during dissolution. Water may be added any time in the process, i.e. before, during or after mixing with a precipitating solvent. It is preferable to add all the required water before mixing with the precipitating solvent, the ratio of water to organic solvent prior to addition of precipitating solvent in the resulting solvent system being from 1:100 to 1:2, preferably 1:20 to 1:5, depending on the organic solvents.

The crystallization of form B can be obtained by mixing with a further organic solvent or a specific precipitating solvent at a temperature up to the boiling point of the specific solvent mixture. It is preferred that the temperature of the mixture during mixing with the precipitating solvent is 0 to +50° C., most preferably +30° C. 20 to +40° C., and for the precipitating solvent preferably to be at ambient temperature before mixing. It is preferred to add the precipitating solvent to the fluvastatin sodium solution. The precipitation solvent may be added continuously or discontinuously, preferably discontinuously in two or three aliquots over a period of up to 8 hours. As the precipitating solvent, an organic solvent may be used, preferably a polar solvent, e.g. ethanol, propan-2-ol, acetonitrile, acetone, ethyl-methyl-ketone, isobutyl-methyl-ketone, methyl-acetate, ethyl-acetate, isopropyl-acetate, most preferably acetonitrile, ethyl-acetate, propan-2-ol or acetone. The amount of precipitating solvent should be such that the concentration of fluvastatin sodium in the resulting mixture is higher than the solubility. The preferred ratio of precipitating solvent to the fluvastatin sodium solution should be in the range 0.5:1 to 10:1 by volume. The water content in the final mixture should preferably be below 10% by volume or otherwise the yield will be unacceptably low or the desired polymorph B may not be formed.

The crystallization may start spontaneously but it has frequently been found desirable to add seeds of fluvastatin sodium form B after the first addition of the precipitating solvent to induce crystallization and to obtain a higher crystallization rate and thus a shorter process time. Mixing, e.g. agitation, is preferable both during mixing of the precipitating solvent and the fluvastatin sodium solution and during the crystallization process. The crystallization should continue for a period to ensure that crystallization is as complete as possible, e.g. 1 to 15 hours, preferably 3 to 8 hours.

The fluvastatin sodium crystals may be separated from the solution, e.g. by filtration or centrifugation, followed by washing with a washing liquid, preferably a solvent mixture in which fluvastatin sodium form B has a very low solubility, most preferably the precipitating solvent. The preferred ratio of washing liquid to the amount of product is 1:1 to 5:1 by weight. It is preferable to cool the slurry to room temperature before separation of the crystals. The separated fluvastatin sodium crystals should be dried to constant weight, e.g. at +30° C. to +50° C., preferably at reduced pressure, for, e.g. 10 to 48 hours. The product from the precipitation process may comprise crystalline needles or agglomerates or a mixture of needles and agglomerates of fluvastatin sodium form B.

The above disclosed processes for preparation of fluvastatin sodium form B are reproducible and give a substantially pure and crystalline substance. This is preferable to lyophilization. The process of crystallization of fluvastatin sodium form B fulfils pharmaceutical criteria and specifications and may reduce batch to batch variability of drug in e.g. crystallinity. Filtration and drying conditions are more favorable for fluvastatin sodium form B than for fluvastatin sodium form A.

In a further aspect, the invention provides a compound obtainable by a process as described above, or, in a broader sense, fluvastatin sodium comprising such a compound.

Medical Use of Fluvastatin Sodium Form B

Fluvastatin sodium form B is useful for lowering the blood cholesterol level in animals, in particular mammals, e.g. humans. It is therefore useful in the prevention of cardiovascular diseases, in particular as a hypercholesterolemic, hyperlipoproteinemic and anti-atherosclerotic agent.

In further aspects, the invention thus relates to the use of fluvastatin sodium form B in the manufacture of a medicament for the treatment of the medical indications mentioned above. The invention also relates to a method for the treatment of such medical indications, said method comprising administering to a mammal, including man, in need of such treatment a pharmaceutically effective amount of fluvastatin sodium form B.

Pharmaceutical Formulations

In another aspect, the invention relates to pharmaceutical compositions comprising fluvastatin sodium form B as active ingredient.

Fluvastatin sodium form B may be formulated for administration in a convenient way and the invention includes all pharmaceutical compositions comprising this particular crystal form adapted for use in human medicine. Oral administration is preferable but other types of administration such as rectal or parenteral (dermal, nasal, tracheal, bronchial, or via inhalation route) administration are of interest.

Examples of formulations are tablets, capsules, pellets, granules, suspensions, solutions and suppositories, which formulations can have immediate-release or modified-release properties. The pharmaceutical compositions are prepared by techniques which are known per se. Preferably, each dosage unit will contain the active ingredient in an amount of 2 mg to 200 mg, and be administered 1 to 4 times per day.

EXAMPLES OF THE INVENTION

1. Preparation of Fluvastatin Sodium Form B
1.1. Preparation of Fluvastatin Sodium Form B by Transformation of Form A in a Slurry Lyophilized fluvastatin sodium form A (4 g) was suspended in propan-2-ol (80 ml) at room temperature, water was added (2 ml) and the initially yellow slurry was stirred for 20 hours with a magnetic stirrer. After approximately 10 hours the slurry had changed in colour to white. The product was filtered off, washed with propan-2-ol (8 ml) and dried at +40° C. under reduced pressure to give 3.6 g fluvastatin sodium monohydrate form B.
1.2. Crystallization of Fluvastatin Sodium Form B (From Free Acid) by Reaction Crystallization Fluvastatin sodium (4 g) was suspended in water (20 ml) at +5° C. Ethyl acetate (25 ml) was added and the product was extracted to the organic phase by addition of a 20% aqueous solution of acetic acid (1 eq) with stirring. The aqueous phase was then separated off. The organic phase was extracted with 20 ml saturated aqueous solution of sodium chloride. First, methanol (12 ml) was added under stirring to the organic phase. Then, an aqueous solution of sodium carbonate (1.9 g, 30%) was added to the organic phase. The solution was heated to +20° C. and the solution was seeded with form B crystals to allow the product to crystallize. After 15 minutes, ethyl acetate (25 ml) was added. After 22 hours the product was filtered off, washed with ethyl acetate (2×5 ml) and dried at +40° C., under reduced pressure, to give 2.9 g fluvastatin sodium form B.
1.3. Preparation of Fluvastatin Sodium Form B by Recrystallization of Lyophilized Form A Lyophilized fluvastatin sodium form A (5 g) was dissolved in a mixture of ethanol (20 ml) and water (2.5 ml) at +40 ° C., and the solution was then stirred for 5 minutes. Acetonitrile (30 ml) was added as a precipitating solvent and the solution was seeded with form B crystals to induce crystallization. After 2 hours, a further quantity of acetonitrile (40 ml) was added. The slurry was stirred for 4 hours at +40° C. and then cooled to room temperature. The product was filtered off, washed with acetonitrile (2×8 ml) and dried at +40° C. under reduced pressure to give 4.6 g fluvastatin sodium monohydrate form B.
1.4. Preparation of Fluvastatin Sodium Form B by Recrystallization of Lyophilized Form A Lyophilized fluvastatin sodium form A (5 g) was dissolved in methanol (20 ml) at +30° C., a small amount of water (2.5 ml) was added and the solution was then stirred for 5 minutes. Propan-2-ol (30 ml) was added as a precipitating solvent and the solution was seeded with form B crystals to induce crystallization. After 2 hours, a further quantity of propan-2-ol (40 ml) was added. The slurry was stirred for 4 hours at +30° C., then a further quantity of propan-2-ol was added (20 ml) and the slurry was allowed to cool to room-temperature. After 2 hours the product was filtered off, washed with propan-2-ol (2×8 ml) and dried at +40° C. under reduced pressure to give 4.5 g fluvastatin sodium monohydrate form B.
1.5. Preparation of Fluvastatin Sodium Form B by Recrystallization of Lyophilized Form A Without Adding Seeds Lyophilized fluvastatin sodium form A (2 g) was dissolved in methanol (8 ml) at +30° C. and the solution was stirred for 5 minutes. The solution was filtered through a glass filter. Water (1 ml) and propan-2-ol (12 ml) were added. The solution was stirred for 21 hours with a magnetic stirrer. The product was filtered off, washed with a mixture of ethanol (2 ml) and propan-2-ol (3 ml) and dried at +35° C. under reduced pressure to give 1.4 g fluvastatin sodium monohydrate form B.
1.6. Preparation of Fluvastatin Sodium Form B by Recrystallization of Fluvastatin Sodium Form B Fluvastatin sodium form B (5 g) was dissolved in methanol (20 ml) at +30° C., a small amount of water (2.0 ml) was added and the solution was then stirred for 5 minutes. Ethyl acetate (40 ml) was added as a precipitating solvent and the solution was seeded with form B crystals to induce crystallization. After 2 hours, a further quantity of ethyl acetate (50 ml) was added and the slurry was stirred for 4 hours at +30° C. The slurry was then cooled to 20° C. in 1 hour. After 2 hours the product was filtered off, washed with propan-2-ol (2×8 ml) and dried at +40° C. under reduced pressure to give 3.9 g fluvastatin sodium monohydrate form B.
1.7. Preparation of Fluvastatin Sodium Form B by Recrystallization of Fluvastatin Sodium Form B Fluvastatin sodium form B (5 g) was dissolved in methanol (20 ml) at +30° C., a small amount of water (2.5 ml) was added and the solution was then stirred for 5 minutes. Acetone (40 ml) was added as a precipitating solvent and the solution was seeded with form B crystals to induce crystallization. After 1 hour, a further quantity of acetone (50 ml) was added and the slurry was stirred for 3 hours at +30° C. The slurry was cooled to +20° C. in 0.5 hour. After 2 hours the product was filtered off, washed with acetone (2×8 ml) and dried at +35° C. under reduced pressure to give 3.5 g fluvastatin sodium monohydrate form B.

1.8. Preparation of Fluvastatin Sodium from B by Spontaneous Crystallization

Lyophilized fluvastatin sodium form A (2 g) was dissolved in acetone (20 ml) at +20° C., a small amount of water (0.8 ml) was added and the solution was then stirred for 6 hours. A thick white slurry was obtained and a further quantity of acetone (20 ml) was added to dilute the system. After 4 hours the product was filtered off, washed with acetone (5 ml) and dried at +30° C. under reduced pressure to give 1.85 g fluvastatin sodium monohydrate form B.

1.9. Crystallization of Fluvastatin Sodium Form A (Example for Comparison)

Lyophilized fluvastatin sodium form A (3 g) was dissolved in a mixture of water (15 ml) and acetone (1 ml) at +40° C. The solution was cooled to +10° C. The resulting slurry was thick and contained soft, needle like crystals. The product could not be isolated because the slurry had unsuitable filtration characteristics.

2. Characterization of Fluvastatin Sodium Form B
1. Infra-red Spectrum

Figure 2:
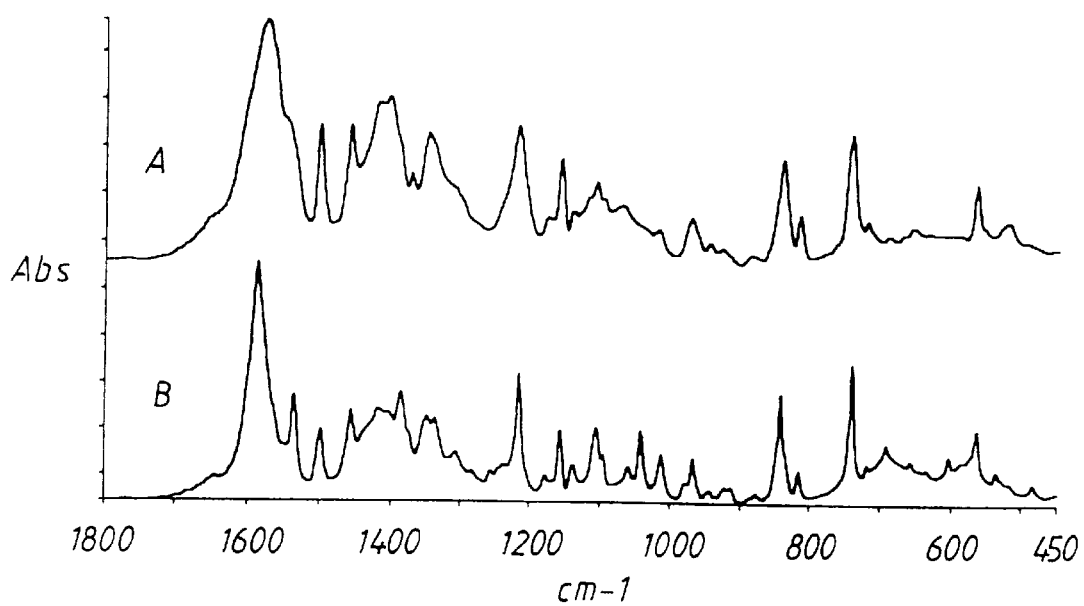
FIG. 2: FT-IR absorbance spectra of fluvastatin sodium (A) form A and (B) form B. Abscissa scale: 1800–450 cm$^{-1}$. Ordinate scale: Absorbance maximum 0.66 at 1577 cm$^{-1}$ for spectrum A, 1.11 at 1587 cm$^{-1}$ for spectrum B.

Fourier-transform infrared (FT-IR) spectra of fluvastatin sodium were obtained from ~1 mg of form A or B in ~250 mg KBr, mortared and pressed into tablets. The spectra, converted to absorbance mode, are shown in FIGS. 1 and 2.

The infrared spectrum of fluvastatin sodium form B showed the main peaks listed in Table 1.

TABLE 1

Vibrational frequencies ($cm^{-1}$) of fluvastatin sodium form B

| | |
|---|---|
| 3343 | 1337 |
| 2995 | 1216 |
| 2937 | 1157 |
| 1587 | 1106 |
| 1536 | 1042 |
| 1499 | 1013 |
| 1456 | 842 |
| 1386 | 741 |
| 1348 | 565 |

The peaks at 3343, 2995, 1587, 1536, 1386, 1337, 1042, and 1013 $cm^{-1}$ are characteristic for form B and are not found in form A.

2.2. X-ray Powder Diffraction (XRPD)

X-ray diffraction analysis was performed according to standard methods, which can be found in e.g. Kitaigorodsky, A. I. (1973), Molecular Crystals and Molecules, Academic Press, New York; Bunn, C. W. (1948), Chemical Crystallography, Clarendon Press, London; or Klug, H. P. & Alexander, L. E. (1974), X-Ray Diffraction Procedures, John Wiley & Sons, New York.

Figure 3:
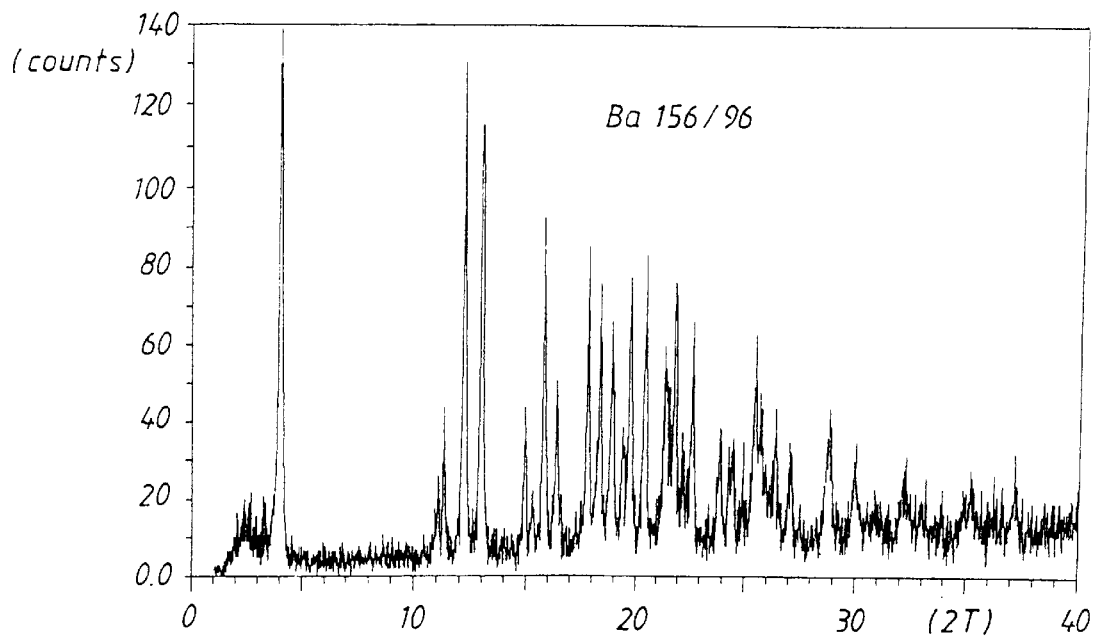
FIG. 3: X-ray powder diffractogram of fluvastatin sodium form A.
Figure 4:
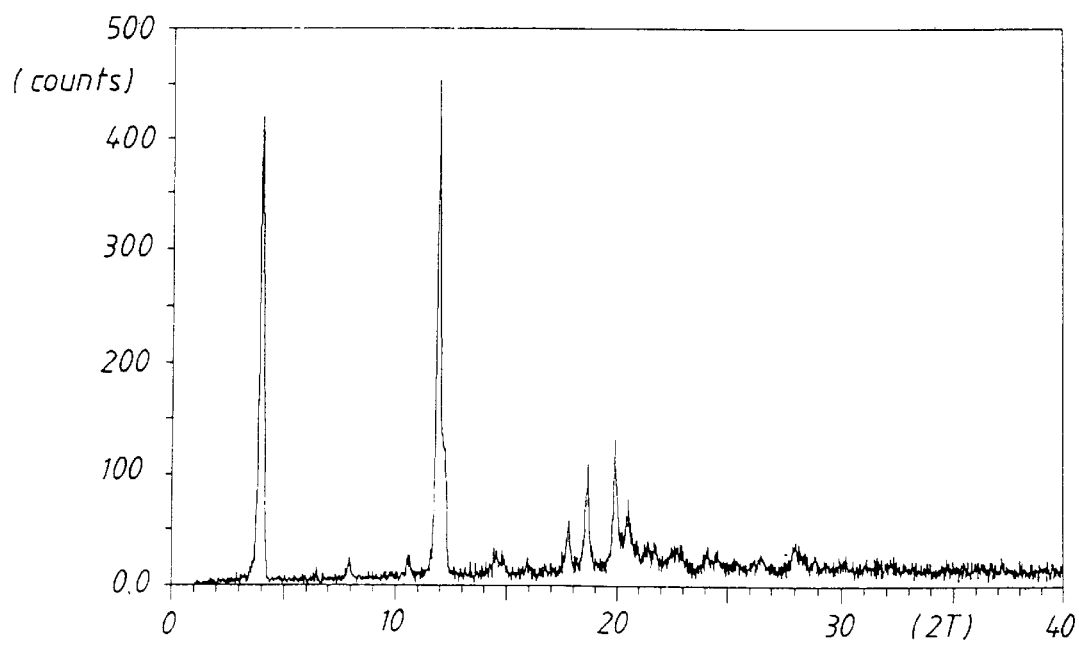
FIG. 4: X-ray powder diffractogram of fluvastatin sodium form B.

The X-ray powder diffraction (XRPD) patterns of fluvastatin sodium forms A and B, obtained in Bragg-Brentano geometry, are shown in FIGS. 3 and 4. The diffraction angles, d-values and relative intensities are shown in Table 2.

Fluvastatin sodium form A shows strong peaks only at 4°, 12° and 19°, while form B shows a large number of relatively strong peaks. This difference indicate a less ordered, two-dimensional structure for form A, and a more ordered structure for form B. This could account for the non-hygroscopic features of form B.

The XRPD diffractograms of both form A and form B have contributions from amorphous material, seen as the broad background, but they differ with respect to degree of crystallinity. Estimation of the degree of crystallinity of the two forms from the intensity in the crystalline part of the diffractograms relative to the total intensity in the diffractograms, gives ~50% crystallinity for form A and ~80% for form B. Thus, fluvastatin sodium form B has a significantly higher degree of crystallinity as compared to form A.

TABLE 2

X-ray powder diffraction angles (2θ, degrees), d-values, and relative intensities, obtained with fixed slits, for fluvastatin sodium forms A and B.

| Form A | | | Form B | | |
|---|---|---|---|---|---|
| 2θ, deg. | d-value, Å | Rel. int. | 2θ, deg. | d-value, Å | Rel. int. |
| 3.965 | 22.265 | 100.0 | 4.063 | 21.728 | 100.0 |
| 7.936 | 11.131 | 0.9 | 11.056 | 7.996 | 2.9 |
| 10.554 | 8.375 | 1.7 | 11.328 | 7.805 | 5.5 |
| 10.645 | 8.304 | 1.5 | 12.210 | 7.243 | 45.2 |
| 11.931 | 7.412 | 44.5 | 12.965 | 6.823 | 34.6 |
| 12.215 | 7.240 | 14.5 | 14.925 | 5.931 | 9.3 |
| 14.496 | 6.106 | 1.1 | 15.277 | 5.795 | 4.5 |
| 14.812 | 5.976 | 0.8 | 15.750 | 5.622 | 18.5 |
| 15.916 | 5.564 | 0.3 | 16.350 | 5.417 | 10.6 |
| 17.769 | 4.988 | 3.2 | 17.760 | 4.990 | 17.6 |
| 18.640 | 4.756 | 5.3 | 18.320 | 4.839 | 14.3 |
| 19.856 | 4.468 | 5.8 | 18.875 | 4.698 | 11.3 |
| 20.518 | 4.325 | 2.9 | 19.396 | 4.573 | 7.0 |
| 20.908 | 4.245 | 1.2 | 19.701 | 4.503 | 13.4 |
| 21.389 | 4.151 | 1.3 | 20.395 | 4.351 | 13.5 |
| 21.722 | 4.088 | 1.1 | 21.329 | 4.163 | 8.5 |
| 22.675 | 3.918 | 0.8 | 21.785 | 4.076 | 15.9 |
| 24.089 | 3.691 | 1.0 | 22.610 | 3.929 | 7.5 |
| 24.533 | 3.626 | 0.5 | 23.868 | 3.725 | 5.4 |
| 26.519 | 3.358 | 0.2 | 24.281 | 3.663 | 3.6 |
| 27.973 | 3.187 | 0.9 | 24.463 | 3.636 | 3.6 |
| 28.861 | 3.091 | | 25.446 | 3.498 | 5.6 |
| | | | 25.655 | 3.470 | 3.6 |
| | | | 26.357 | 3.379 | 3.3 |
| | | | 27.040 | 3.295 | 2.8 |
| | | | 28.747 | 3.103 | 3.4 |
| | | | 29.940 | 2.982 | 2.8 |
| | | | 32.165 | 2.781 | 1.6 |
| | | | 35.173 | 2.549 | 1.0 |
| | | | 37.131 | 2.419 | 1.3 |

The unit cells of forms A and B were estimated from the crystalline part of their respective XRPD diffractograms. This gave the following unit cell parameters, corresponding to triclinic unit cells, listed in Table 3. The molar mass M was calculated on the basis of monohydrate for both forms, and the calculated density is based on a value of 2 for Z.

TABLE 3

Unit cell parameters of fluvastatin sodium form A and B, estimated from the XRPD patterns.

|   | Form A | Form B |
|---|---|---|
| a | 6.02 Å | 6.08 Å |
| b | 23.0 Å | 22.3 Å |
| c | 8.48 Å | 8.48 Å |
| α | 101.7° | 87.4° |
| β | 89.8° | 91.1° |
| γ | 97.4° | 103.0° |
| V | 1140 Å$^3$ | 1120 Å$^3$ |
| M | 451.5 g/mol | 451.5 g/mol |
| $\delta_{calc}$ | 1.315 g/cm$^3$ | 1.339 g/cm$^3$ |

The XRPD pattern of form A shows strong peaks at 3.965°, 11.931°, 12.215°, 17.769°, 18.640°, 19.856°, and 20.518°, whereas the remaining peaks are rather weak.

It was found that after wetting of a sample of form A, the XRPD pattern changed into a pattern with only the peaks at 3.965°, 7.936°, 11.931°, 15.916°, and 19.856°. These peak values constitute a progression, being multiples of ~4°. Such a pattern, with few strong peaks, and with a progression of peaks, is characteristic for a layered crystal structure.

It is thus probable that fluvastatin sodium form A has a layered crystal structure. In this layered crystal structure, the layers are probably alternately polar and non-polar. The Na$^+$ cations and the crystal water form a polar, hydrophilic layer, towards which the organic fluvastatin anions turn their hydrophilic COO$^-$ end. The aromatic, hydrophobic end of the fluvastatin anions are packed towards each other in the hydrophobic layers at van der Waals distance.

The distance between the layers is 23.0 Å. The fact that there are few strong bands in the XRPD pattern, except for the peaks corresponding to the layers, indicates that there is a low degree of ordering within the layers.

The XRPD pattern of form B shows a much larger number of relatively strong peaks. The difference in the XRPD patterns between the A (before wetting) and B forms indicates a higher degree of ordering of the crystal structure in the B than in the A form. The B form also seems to have a layered crystal structure, but the degree of ordering within the layers is higher than for the A form, as seen from the larger number of relatively strong peaks in the B form.

A possible interpretation of the change in the diffractogram of form A upon wetting is that the distance between the layers is approximately constant, but the degree of ordering in the layers, especially in the hydrophilic layers, decreases upon water uptake.

The hygroscopicity of form A seems to be a result of the relatively high energy in the hydrophilic part of the fluvastatin sodium molecule, and its strive for lower energy. After uptake of large amounts of water, the ordering within the layers disappears, mainly in the hydrophilic layers. This leads to an XRPD pattern with no other peaks than those corresponding to the interlayer distance.

In form B, the hydrophilic layers are ordered and stable. They do not need to take up water. Form B is thus non-hygroscopic.

2.3. Water sorption/desorption Profiles

The hygroscopicity of fluvastatin sodium was determined with a DVS Automatic Water Sorption Analyser at 25° C. The sorption/ desorption of the substance was tested at different percentages of relative humidity by a stepwise change of the humidity (40, 60, 80, 95 and 0% RH). The results are shown in FIG. 5.

Fluvastatin sodium form A showed a linear uptake of water. At 95% relative humidity, the weight increase is approximately 35%. Amorphous fluvastatin sodium showed a water sorption similar to fluvastatin form A.

Fluvastatin sodium form B was found to be non-hygroscopic. The weight increase up to 80 % relative humidity was not more than 1% and at 95% relative humidity the water sorption corresponded to about 4%.

3. Stability 3.1. Determination of Degradation Products

In the following experiments, degradation products of fluvastatin sodium were quantified by high-performance liquid chromatography, using a reversed-phase system with a Hypersil ODS column (5 μm, 50*4.6 mm). The compounds were eluted with a gradient ranging from 0.5 to 0.2% of tetramethyl ammonium hydroxide; 19 to 30% of acetonitrile; and 28 to 45% of methanol. Products were detected at 305 and 365 nm.

3.2. Photostability

Thin layers of fluvastatin sodium forms A and B were spread out in open petri-dishes. The substances were exposed to radiation (Xenonlamp, 150 klux, 280–830 nm) for 24 hours. The amount of undegraded fluvastatin sodium after 24 hours light-exposure is shown in Table 4. Fluvastatin sodium form A changed in colour to dark yellow after 24 h of light-exposure. Form B did not change its colour after 24 h exposure.

TABLE 4

|   | 0 h | 24 h |
|---|---|---|
| Form A | 99.6 | 88.2 |
| Form B | 99.7 | 98.9 |

3.3. Accelerated Stability Testing at Controlled Temperature and Relative Humidity Accelerated stability tests were performed to study the rate of chemical degradation or physical change of the test substances by using exaggerated storage conditions. The results are considered as relevant also for assessing longer term chemical effects at non-accelerated conditions.

Thin layers of Fluvastatin sodium, forms A and B, were spread out in plastic beakers, without lids, and placed in cupboards with controlled temperature and relative humidity (RH). Table 5 shows the amounts of undegraded fluvastatin sodium after 6 months at +40° C. (75% RH) and at +50° C. (ambient RH).

TABLE 5

|   | Start | +40° C. 75% RH | +50° C. ambient RH |
|---|---|---|---|
| Form A | 99.6 | 84.4 | 95.5 |
| Form B | 99.7 | 99.3 | 99.4 |

3.4. Conclusions

The results from the experiments described in sections 3.2 and 3.3 indicate that fluvastatin sodium form B provides improved stability compared with the lyophilized substance, form A, under the stressed conditions that have been investigated (light, high humidity and raised temperature).

It is claimed:

1. Fluvastatin sodium form B having an infra-red spectrum showing peaks at 3343, 2995, 1587, 1536, 1386, 1337, 1042, and 1013 cm$^{-1}$.

2. The compound according to claim 1, wherein fluvastatin sodium form B is in a substantially crystallographically pure form.

3. The compound according to claim 1, wherein fluvastatin sodium form B provides an X-ray powder diffraction pattern exhibiting substantially the following d-values and relative intensities:

| d-value, Å | re. Int. |
|---|---|
| 21.73 | 100.0 |
| 7.80 | 5.5 |
| 7.24 | 45.2 |
| 6.82 | 34.6 |
| 5.93 | 9.3 |
| 5.80 | 4.5 |
| 5.62 | 18.5 |
| 5.42 | 10.6 |
| 4.99 | 17.6 |
| 4.84 | 14.3 |
| 4.70 | 11.3 |
| 4.57 | 7.0 |
| 4.50 | 13.4 |
| 4.35 | 13.5 |
| 4.16 | 8.5 |
| 4.08 | 15.9 |
| 3.93 | 7.5 |
| 3.72 | 5.4 |
| 3.66 | 3.6 |
| 3.64 | 3.6 |
| 3.50 | 5.6 |
| 3.47 | 3.6. |

4. A process for the preparation of the compound according to claim 1, wherein fluvastatin sodium form B is precipitated from a mixture comprising at least one organic solvent and water and isolated therefrom.

5. The process according to claim 4, which comprises the steps:
   (a) partly dissolving a non-B form of fluvastatin sodium in the organic solvent and water mixture; and
   (b) stirring until fluvastatin sodium form B is obtained.

6. A process for the preparation of the compound according to claim 1, wherein fluvastatin sodium form B is formed in a mixture comprising an organic solvent and water by reaction crystallization employing a sodium compound to react with fluvastatin.

7. The process according to claim 6, wherein the sodium compound is sodium hydroxide or sodium carbonate.

8. A process for the preparation of the compound according to claim 1, wherein fluvastatin sodium form B is caused to crystallize from a mixture comprising an organic solvent and water in the presence of an additional precipitating solvent.

9. The process according to claim 8, which comprises the steps:
   (a) dissolving fluvastatin sodium in a first organic solvent or a mixture comprising a first organic solvent and water;
   (b) adding water if required and a polar precipitating organic solvent so as to obtain crystallization of fluvastatin sodium form B, optionally following seeding with crystalline fluvastatin sodium form B; and
   (c) isolating and drying the crystalline fluvastatin sodium thus obtained.

10. The process according to claim 9, wherein fluvastatin sodium is initially dissolved in an organic solvent selected from methanol, ethanol or a mixture thereof with water.

11. The process according to claim 9 or 10, wherein fluvastatin sodium is dissolved in the organic solvent or mixture in an amount of 2 to 20 ml/g.

12. The process according to claim 8 or 9, wherein all the water is included in the solvent system before adding the precipitating solvent and wherein the ratio of water to organic solvent prior to addition of the precipitating solvent is 1:100 to 1:2.

13. The process according to claim 8 or 9, wherein the water content in the final mixture from which crystallization of fluvastatin sodium form B occurs is below 10% by volume.

14. The process according to claim 8 or 9, wherein the precipitating solvent is selected from the group consisting of acetonitrile, propan-2-ol, ethyl acetate and acetone.

15. The process according to claim 8 or 9, wherein the precipitating solvent is added in the range 0.5:1 to 10:1 by volume of fluvastatin sodium solution.

16. Fluvastatin sodium form B obtainable by a process as defined in any one of claims 4 to 10.

17. Fluvastatin sodium form B according to any one of claim 1 or 2 for use in therapy.

18. A pharmaceutical composition comprising fluvastatin sodium form B according to any one of claim 1 or 2 as active ingredient and a pharmaceutically acceptable diluent or carrier.

19. A method for the treatment of a cardiovascular disease, comprising administering to a mammal, in need of such treatment a pharmaceutically effective amount of fluvastatin sodium according to any one of claim 1 or 2.

20. A pharmaceutical formulation for the treatment of a cardiovascular disease, comprising fluvastatin sodium according to any one of claim 1 or 2 and a pharmaceutically acceptable diluent or carrier.

21. The compound according to claim 2, wherein the fluvastatin sodium form B has no more than 5% of any other crystalline form of fluvastatin.

22. The method according to claim 19, wherein the cardiovascular disease is hypercholesterolemia, hyperlipoproteinemia or artherosclerosis.

23. The pharmaceutical composition according to claim 20, wherein the cardiovascular disease is hypercholesterolemia, hyperlipoproteinemia or artherosclerosis.

* * * * *

UNITED STATES PATENT AND TRADEMARK OFFICE
CERTIFICATE OF CORRECTION

PATENT NO. : 6,124,340
DATED : September 26, 2000
INVENTOR(S) : Karol Horvath

It is certified that error appears in the above-identified patent and that said Letters Patent is hereby corrected as shown below:

In claim 17, column 12, line 29, delete "claim 1 or 2" and substitute therefor --claims 1 to 3--.

In claim 18, column 12, line 31, delete "claim 1 or 2" and substitute therefor --claims 1 to 3--.

In claim 19, column 12, line 37, delete "claim 1 or 2" and substitute therefor --claims 1 to 3--.

In claim 20, column 12, line 40, delete "claim 1 or 2" and substitute therefor --claims 1 to 3--.

Signed and Sealed this

Twenty-fourth Day of April, 2001

Attest:

NICHOLAS P. GODICI

Attesting Officer

Acting Director of the United States Patent and Trademark Office